(12) United States Patent
Douglas-Hamilton et al.

(10) Patent No.: US 9,040,272 B2
(45) Date of Patent: May 26, 2015

(54) APPARATUS AND METHOD FOR LIVING CELL MANIPULATION

(75) Inventors: Diarmaid H. Douglas-Hamilton, Beverly, MA (US); Thomas G. Kenny, Ipswich, MA (US)

(73) Assignee: Hamilton Thorne, Inc., Beverly, MA (US)

( * ) Notice: Subject to any disclaimer, the term of this patent is extended or adjusted under 35 U.S.C. 154(b) by 0 days.

(21) Appl. No.: 13/158,843

(22) Filed: Jun. 13, 2011

(65) Prior Publication Data

US 2011/0306108 A1  Dec. 15, 2011

Related U.S. Application Data

(60) Provisional application No. 61/354,479, filed on Jun. 14, 2010.

(51) Int. Cl.
| C12N 13/00 | (2006.01) |
| C12M 1/00 | (2006.01) |
| C12M 1/36 | (2006.01) |
| C12N 5/00 | (2006.01) |
| C12M 1/42 | (2006.01) |

(52) U.S. Cl.
CPC ............. *C12N 13/00* (2013.01); *C12M 35/02* (2013.01)

(58) Field of Classification Search
None
See application file for complete search history.

(56) References Cited

U.S. PATENT DOCUMENTS

| 5,321,715 | A * | 6/1994 | Trost ............................... 372/69 |
| 6,346,101 | B1 | 2/2002 | Alfano et al. |
| 2004/0167499 | A1 | 8/2004 | Grove et al. |
| 2007/0291798 | A1 | 12/2007 | Kenny et al. |
| 2009/0000665 | A1 | 1/2009 | Oshemkov et al. |

FOREIGN PATENT DOCUMENTS

| JP | 2004-514150 A | 5/2004 |
| JP | 2006-126344 A | 5/2006 |
| JP | 2007-163738 A | 6/2007 |
| JP | 2009-537024 A | 10/2009 |
| WO | 01/50963 A1 | 7/2001 |
| WO | 2008/156475 A1 | 12/2008 |

OTHER PUBLICATIONS

Germond et al., 1995, Fertil. Steril. 64:604-611; abstract p. 1.*
Chen et al., 2006, Physical Review Letters 96:034505.1-034505.4.*
Le Gac et al 2007, Lab Chip 7:1666-1671.*
Petrova-Mayor et al 2008, Applied Optics 47:1522-1534.*
Venugopalan et al 2002, PRL 88:078103-1 to 4.*
International Search Report issue don Oct. 18, 2011 in International Appln. No. PCT/US2011/040169.

* cited by examiner

*Primary Examiner* — Christopher M Babic
*Assistant Examiner* — Kelaginamane T Hiriyanna
(74) *Attorney, Agent, or Firm* — Stroock & Stroock & Lavan LLP (57) ABSTRACT

The present invention provides a method and system for using eye-safe infrared energy from a Class I laser to manipulate cells in culture. The laser energy produces one or more phase boundary propulsion events, which generate hydrodynamic forces sufficient to manipulate cells at the focal point.

14 Claims, 8 Drawing Sheets

APPARATUS AND METHOD FOR LIVING CELL MANIPULATION

RELATED APPLICATIONS

This application claims the benefit of, and priority to, U.S. Provisional Application No. 61/354,479, filed Jun. 14, 2010, entitled "Apparatus and Method for Living Cell Manipulation," which is incorporated herein in its entirety by this reference.

BACKGROUND

Methods for moving or manipulating living cells are essential tools that enable research directed to therapies relating to stem cells, in vitro fertilization, cell and tissue culture, tissue regeneration and similar fields. For example, widely used stem cells, whether derived from embryos (ES), induced pluripotent stem cells (IPS), cord blood cells, adult cells such as skin or other tissues, have great promise for therapeutic action because of the ability of these pluripotent cells to differentiate into different terminal cell types. While this ability has enabled recent developments in tissue replacement therapy, manipulating stem cell colonies can be very time consuming and difficult. Cell manipulations that enable propagation of stem cells—in particular, isolating cells or cell culture colonies for transport ("passaging")—remain highly laborious and technically demanding (see, e.g., Cooke, J. A. and Minger, S. L. *Culture of Human Stem Cells* Ch. 2, 2007, incorporated herein by reference).

Fewer methods exist for moving cells maintained in culture, as confluent layers ("sheets") or otherwise adherent to the surface of a tissue culture dish pose difficult problems if these cells need to be moved or manipulated. Stem cells in particular exist in colonies grown on substrates surrounded by nutrient-rich growth medium, frequently in Petri dishes. Normal growth of these cells in culture requires passaging—division of cells in to another chamber containing fresh growth medium. For some cell types, it may be further desirable to isolate a small population of cells from a larger population, or a portion of a layer, and transfer those cells to a different location for further testing, study or treatment.

Maintaining undifferentiated stem cells in long term culture presents a special problem, however. Stem cell colonies tend to differentiate over time in vitro. Therefore to maintain the stem cell line, or to significantly multiply the number of cells, the undifferentiated portions (or selected colonies) must be isolated and passaged to new containers. Ideally, excision and passaging should be done without compromising the colony, that is, without killing large numbers of cells. Although cell passaging using enzymes like trypsin or collagenase to release adherent cells from their substrate has been in routine use for decades, use of enzymes in stem cell cultures is particularly disfavored because of the increased risk of genetic alterations.

Non-enzymatic, mechanical methods have been described for achieving the goal of excising or cutting cells from the substrate on which they are grown. For example, it is well known in the art that cells can be excised from a confluent layer by making scoring or cutting the layer with a finely drawn glass micropipette. After cutting, the layer "pieces"—small clusters of cells—can be lifted off of the surface and placed in a different environment. Manual cutting using drawn glass micropipettes is preferred because this method minimizes the chance of genetic alteration of stem cells.

Another mechanical method for separating cells involves the use of piezoelectric microknives, for example, the Micro-Chisel Piezo-Power Microdissection (PPMD) system (see, e.g., Harsch, M. A. et al. *Am. J. Pathol.* 158:1985-90, 2001). PPMD employs a sharpened tungsten needle as a microscopic knife that oscillates from small piezoelectric vibrations to dissect cells from surrounding tissue. While simple, this method lacks precision and accuracy on a cellular level, and undoubtedly kills or damages cells in large numbers due to lateral vibrations and contact with the micropipette or knife.

While PPMD may be a suitable technique in certain circumstances, in other applications it will be particularly important to avoid mechanical damage. This is especially true in cases where a relatively few number of high value cells must be isolated and cannot be lost to excessive tissue damage. In other cases, cell damage or destruction may release harmful chemicals into the tissue culture medium that could lead to an adverse impact on cell growth, physiology, or function. Another disadvantage to these physical methods for cell manipulation is that cutting devices can introduce foreign materials into the cell colony, possibly contaminating or otherwise compromising the integrity of the culture.

Lasers present an alternative means for the micromanipulation of living cells and tissue. The art has disclosed infrared laser "traps," sometimes referred to as "optical tweezers," that use forces of radiation pressure to manipulate entire living cells or organelles within cells (see, e.g., Ashkin, A. and Dziedzic, J. M. *Nature* 330:769-71, 1987). Lasers have also been used to "weld" detached retinas, to sculpt the cornea to achieve different optical focusing in myopic patients, and to eliminate unwanted cells in a culture.

Lasers have been also useful for cutting biological material such as fixed cells in tissue samples. "Laser scissors" have been developed where cells (or a portion thereof) can be literally cut by a laser beam acting as a scalpel. Lasers can be used to create micron-sized pores in cell membranes in a process called optoporation. These small pores seal quickly and do not result in permanent damage, but while open, the pore might permit chemicals to enter the inside of the cell that are normally excluded by the cell membrane, including large molecules like DNA that, if introduced, might change the genetic makeup of the cell. Laser manipulation has also proven useful for the assisted hatching of human eggs in fertility assistance programs and clinics. Laser ablation, for example, using the ZILOS-tk ($\lambda$=1450 nm), has been used in vitro to thin or even remove a small area of the zona pellucida surrounding embryos; this procedure is used to enhance implantation of the new embryo without damaging it, and to enable a portion of the embryo trophectoderm to emerge and be removed for trophectoderm pre-implantation genetic diagnosis (see, e.g., Pangalos, C. G. et al. *Fetal Diagn. Ther.* 24:334-339, 2008).

Lasers avoid many problems associated with the enzymatic or mechanical methods for cell manipulation described above. There is no contamination since the laser cutting beam is non-material and cannot introduce any foreign material into the growth chamber. Microscope-based laser systems using an automatic stage can be set up to divide specimens into small areas with micron precision for subsequent passaging, in patterns that can be re-run automatically as necessary.

However, because of the high amounts of energy contained in a laser beam, one problem in laser manipulation is heat generation and damage to adjacent structures. Lasers used in cell manipulation are often operated in short sub-microsecond pulses to deliver brief doses of energy. The overall energy to the system can be finely tuned by changing one or more parameters such as the laser power, the duration of the pulse, and the number of pulses. Local heating will increase as the power and the overall pulse duration increase.

According to International Standard IEC 60825-1 Amendment 2 (see also 21C.F.R. §1040.10), which is accepted by the Food and Drug Administration (see, e.g., FDA Laser Notice No. 50), lasers are classified by their ability to cause biological damage to the eye or skin during use. Based on laser wavelength, beam power, and pulse duration, classifications proceed from Class I, safe under all conditions of normal use, to Class IV, high power lasers that can burn the skin or ignite combustible materials, in addition to causing potentially devastating and permanent eye damage. Class I lasers are generally believed to have insufficient power for cutting or burning.

A laser microdissection system called PALM® uses a UV $N_2$ laser ($\lambda$=337 nm, 3 ns pulse duration, with peak pulse power in excess of 10 kW) to provide a system for the retrieval of selected cell populations and single cells from tissue sections (see, e.g., Vogel, A. et al. *Meth. Cell Biol.* Vol. 82, Ch. 5, 2007). A frequency-tripled Nd:YAG laser at 355 nm has also been used for this purpose. Pulses from the UV laser are focused through the microscope to cause laser ablation of cells and tissue in a tissue section. The sample is generally not under a medium as it is necessary to minimize the effective sample mass. PALM is thought to operate through a photochemical mechanism that breaks down biological material into atoms that are blown away from the sample at supersonic velocities. This cutting action is restricted to a tiny focal spot of the laser (<1 µm), leaving adjacent material like neighboring cells or nearby nucleic acids and proteins intact (see, e.g., Schutze, K. et al. *Cell. Mol. Biol.* (Noisy-le-grand) 44:735-746, 1998). A second pulse propels the cut-out sample into a collection device.

Despite these achievements, the use of UV photons carries the risk of actinic effects, and the Class III or Class IV lasers required to produce the extremely short and intense pulses required to cut biological materials are potentially hazardous and costly to operate.

Therefore, the need exists in the art to provide a reliable, cost-effective Class I laser-based system and method for safely manipulating cells (e.g., cutting cells, excising sheets of cells for further examination or manipulation, etc.).

SUMMARY

The present invention provides a method and system for using eye-safe infrared energy from a Class I laser to manipulate cells in culture. The laser energy produces one or more phase boundary propulsion events as superheated water in the aqueous cell medium changes to vapor and generates hydrodynamic forces sufficient to manipulate cells at the focal point.

In one aspect, the invention provides a method of inducing phase boundary propulsion (PBP) at a focal point in an aqueous medium, comprising providing infrared energy having a wavelength greater than 1400 nm to the focal point in the medium using a laser and an objective lens.

In one or more preferred embodiments, the laser is a Class I laser.

In various embodiments, the laser energy has a wavelength between 1400 and 1500 nm.

In certain embodiments, the laser energy has a wavelength of about 1450 nm. In some embodiments, the laser energy has a wavelength between 1400 and 1450 nm. In still further embodiments, the laser energy has a wavelength between 1410 and 1430 nm.

In other embodiments, the laser energy has a wavelength between 1850 and 1920 nm.

In some embodiments, the aqueous medium comprises a plurality of suspended cells. In certain embodiments, the cells are stem cells.

In various embodiments, the PBP repositions one or more cells.

In some embodiments the PBP penetrates a membrane of one or more cells. In certain embodiments, said penetrating further comprises incorporating exogenous DNA into the cells.

In some embodiments, the method further comprises moving the focal point through the medium, and repeating said providing. In certain embodiments, said moving is performed at a frequency less than or equal to 10 frames per second.

In some embodiments, said providing comprises providing a plurality of pulses between 100 and 1000 Hz. In certain embodiments, said providing comprises providing about 200 pulses per second.

In certain embodiments, the laser energy is provided in sequential pulses, a first pulse having a wavelength between 1450 and 1490 nm and a second pulse having a wavelength between 1400 and 1430 nm.

In some embodiments, said providing comprises providing the infrared energy in one or more pulses of duration less than 4 ms. In certain embodiments said providing comprises providing the infrared energy in one or more pulses of duration between 50 and 500 µs. In still further embodiments, said providing comprises providing the infrared energy in one or more pulses of duration of about 150 µs.

In another aspect, the invention provides a system for inducing phase boundary propulsion at a focal point in an aqueous medium, comprising a laser providing infrared energy having a wavelength greater than 1400 nm, and an objective lens.

In one or more preferred embodiments the objective lens is 40× or 20×.

In some embodiments, a power of the laser is between 200 and 400 mW. In certain embodiments, a power of the laser is about 300 mW.

In certain embodiments, the laser provides the infrared energy in a plurality of repeated pulses and a mean power of the system averaged over the pulses is less than 90 mW.

In various embodiments, the system further comprises a microscope having a mechanical stage, a turret, at least one of an eyepiece and a camera, and a dichroic mirror, said laser mounted to the turret, and said mirror reflecting the infrared energy from the laser to the stage and reflecting visible light into the at least one of the eyepiece and the camera.

In one or more preferred embodiments, the laser is permanently fixed to the objective.

Additional features and advantages of the present invention are described further below. This summary section is meant merely to illustrate certain features of the invention, and is not meant to limit the scope of the invention in any way. The failure to discuss a specific feature or embodiment of the invention, or the inclusion of one or more features in this summary section, should not be construed to limit the invention as claimed.

BRIEF DESCRIPTION OF THE FIGURES

The foregoing summary, as well as the following detailed description of the preferred embodiments of the application, will be better understood when read in conjunction with the appended drawings. For the purposes of illustrating the device of the present application, there is shown in the drawings preferred embodiments. It should be understood, however, that the application is not limited to the precise arrangements and instrumentalities shown.

DETAILED DESCRIPTION OF THE INVENTION

Lasers have long been known to be useful tools for cutting materials, metals and films. Although lasers have proven to be similarly useful for cutting biological materials, the high energy of laser systems creates significant safety issues for the user. Perhaps most significantly, light of wavelength less than 1400 nm, which includes the visible light range, can penetrate the cornea of the eye. When focused through the lens, the highly coherent laser light in a focused spot can irreversibly burn local regions of the retina. Even very short pulses of highly energetic light can cause permanent retinal damage.

In addition, shorter wavelengths of light, such as those in the blue and ultraviolet range, carry enough energy to disrupt chemical bonds and generate free radicals capable of causing widespread tissue damage. Chemical effects resulting from photonic radiation are referred to as "actinic" effects, and in general, these effects are considered to be damaging to biological tissues and important molecules like DNA. When manipulating living cells, it is therefore very desirable to minimize the possibility of irreversible cellular damage and, preferably, use wavelengths whose photons are too low in energy to cause actinic effects. Longer laser wavelengths can help achieve the goal of minimizing actinic effects.

Another related factor relevant to laser safety is the laser class. As discussed above, Class I lasers are generally considered safe, and require few precautions for routine use. For a given beam strength, usually measured in watts (W), longer wavelength lasers will tend to be safer. Because water is the predominant component of biological materials, the interaction of the laser beam with water is a significant determinant of the effect of the laser on living cells. Energy from photons with wavelengths greater than 1400 nm (in the near- to mid-infrared (IR) portion of the light spectrum) is efficiently absorbed by water molecules as vibrational energy (from intramolecular stretching and bending) and then quickly released as heat. In water and aqueous media, the beam energy rapidly attenuates over a very short distance. Photons in this wavelength range are too strongly absorbed to reach the retina through the vitreous humor. Similarly, the energy of λ>1400 photons is too low to cause actinic effects. Because of these properties, Class I lasers with λ>1400 nm (e.g., in the 1400-1500 nm wavelength range) are typically classified as "eye safe."

Until now, Class I lasers within the 1400-1500 nm range have not been effective tools for cutting biological materials. While near-infra-red lasers have been used as laser tweezers, short-wavelength UV repetitive-pulse lasers have been applied to cutting cells and manipulating cell colonies. These high intensity beams generally require only very short pulse durations, typically 3 ns or less, and power during pulse on the order of 10 kW (30P), with multiple pulses producing the desired effect. The highly intense local irradiation from photons in a focused UV laser beam provides sufficient energy to break chemical bonds in a very small region. However, scattered UV radiation can affect local cells and induce chemical changes which can compromise the cells in the surrounding volume. The present invention uses Class I infrared radiation, exclusively in the eye-safe region. Less intense beams pulsed for longer times enable effective cell colony cutting/manipulation.

As mentioned above, water can be a strong absorber of IR radiation. Resonance between photon energy and various overtones and superpositions of the $H_2O$ molecular symmetric and asymmetric stretch and the bending vibrational modes lead to great variations in absorbance in the wavelength range 1000<λ<2000 nm. There is a strong absorbance peak at λ=1450 nm corresponding to the symmetrical (v1) and asymmetrical (v3) fundamental vibrational modes. Water absorption therefore greatly limits the transmission of laser light at λ=1450 nm.

If the medium is highly absorbant, only a small fraction of the IR beam arrives at its target after transmission through the medium. To deliver the energy of a highly-absorbed IR laser beam to a cell, contact fibers have been used in the past to fiber-optically guide beams directly to the target. However this method does not allow the beam to be focused, and, like the mechanical methods described above, introduces external material (e.g., the optical fiber) into the growth chamber, risking contamination.

Laser beams at appropriate wavelength, concentrated to a focal point using microscope optics, can overcome the energetic decrease due to water absorption. This is particularly useful in cell cultures, where an optically clear substrate (like a Petri dish) can transmit a converging light beam formed through the optics of an inverted microscope to pass to the target. At the focal point, the energy of the beam is at its strongest and can affect cells and materials nearby. The beam focus is preferably kept within 15 μm of the floor of the dish. Although an inverted microscope is generally used for this purpose, the same principle applies for upright microscopes. Lower power IR lasers of appropriate wavelength and focal intensity can deliver sufficient energies for cell manipulation purposes, and avoid the reliance on UV lasers which carry the host of undesirable characteristics described above.

The absorption of radiation in the aqueous medium and the associated heating effects have been discussed, for example, by Douglas-Hamilton and Conia and by Tadir and Douglas-Hamilton (see Douglas-Hamilton, D. H. and Conia, J. *J. Biomed. Optics* 6:205-213, 2001 and Tadir, Y. and Douglas-Hamilton, D. H. *Meth. Cell Biol*. Vol. 82, Ch. 14, 2007, both incorporated herein by reference). For example, when using IR lasers (>100 mW, λ=1480, 100-3000 µs pulse length) to manipulate the zona pellucida of embryos, the aqueous medium becomes significantly superheated, rapidly reaching temperatures greater than 200° C. (e.g., about 300° C.). At such elevated temperatures, water is strongly metastable. If a nucleation site is present, water at these temperatures will change from liquid to vapor phase with near explosive speed. When no nucleation site is present, however, at the end of the pulse superheated water will rapidly cool below the boiling point (e.g., within 10-100 µs) before explosive evaporation. This process—superheating followed by cooling—occurs under normal pulse-laser conditions, in which energy-delivering pulses are interrupted by periods of cooling.

If, however, a nucleation site or additional energy is provided to superheated water, boiling can take place, that is, a phase transition from liquid water to water vapor can occur. Phase transition in superheated water leads to the formation of a rapidly moving phase boundary between bubble and liquid, which can propel local objects such as cells (phase boundary propulsion). Following expansion, rapid cooling of the bubble occurs due to exposure to a larger volume of cooler water. This rapid cooling leads to re-condensation and collapse of the vapor bubble within a few microseconds. This cycle of heating and cooling superheated water to effect liquid-vapor phase transitions that move matter in accordance with the instant invention is referred to herein as "phase boundary propulsion" (PBP). In some embodiments of the invention, the PBP bubble has a lifetime of less than 30 µs.

Figure 1A:
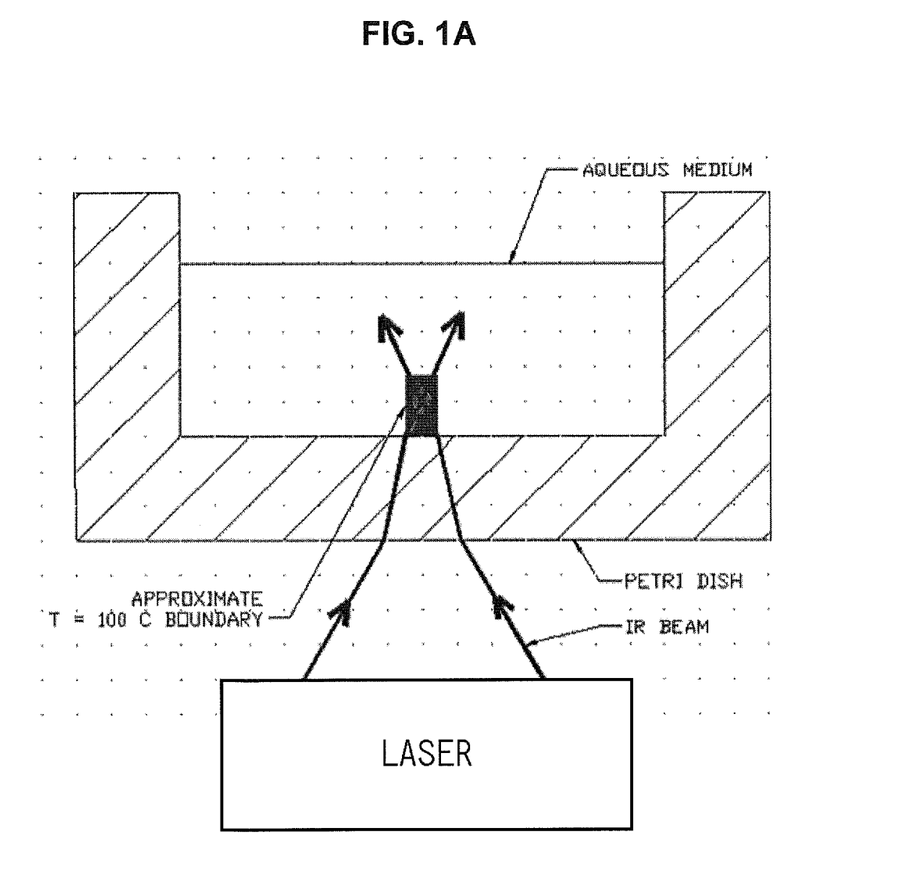
FIG. 1A. Schematic diagram of the first stage of phase boundary propulsion (not to scale). Incident beams from an IR laser are focused on a focal point in the aqueous medium in a Petri dish, around which water becomes superheated to temperatures above the boiling point.
Figure 1B:
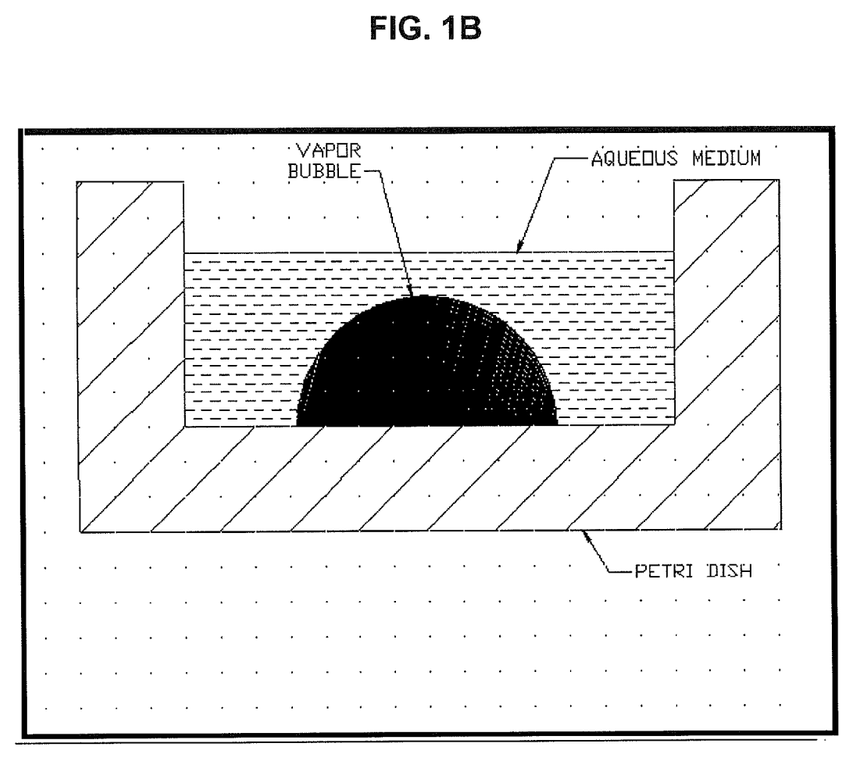
FIG. 1B. Schematic diagram showing the large vapor bubble created after triggering phase change of the superheated water. Vapor bubble formation causes nearby objects to move in response to hydrodynamic forces.
Figure 1C:
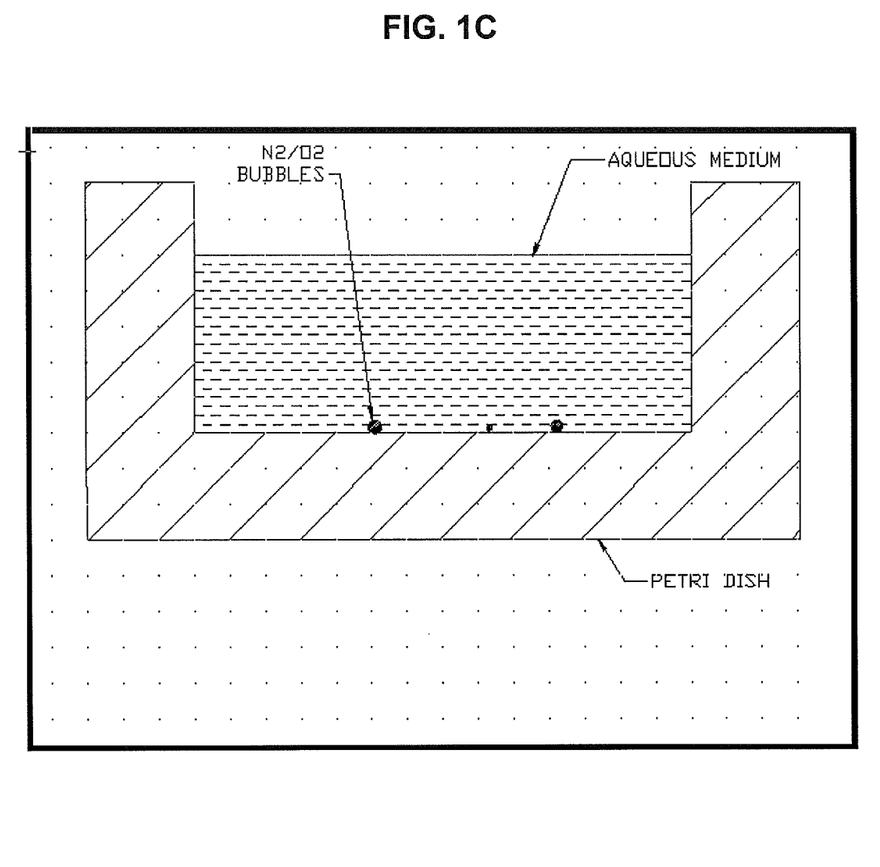
FIG. 1C. Following collapse of the vapor bubble, small bubbles of ex-solved gases ($N_2$, $O_2$) temporarily remain until re-dissolved into the aqueous medium.

A schematic illustration of PBP effects is provided in FIGS. 1A through 1C. FIG. 1A shows a schematic, not-to-scale drawing of the components of an apparatus according to the present invention. Collimated light from a laser of suitable wavelength and power is focused through an objective to produce superheated water. This results in a sudden phase change. Examples of suitable systems for providing laser light according to the present invention include the ZILOS-tk and XYClone laser systems provided by Hamilton Thorne, Inc. which have a laser fixed to an objective and mountable onto the turret of a microscope. These and other suitable examples are described in U.S. Pat. No. 7,072,377 and U.S. Patent Application Publication Nos. US 2007/0291798, 2009/0316259, and US 2010/0118395, each incorporated herein by reference in its entirety. As shown in FIG. 1A, light from a laser heats a region near the focal point, up to temperatures above the liquid boiling point. Following a latency interval a large fraction of the superheated liquid suddenly vaporizes, forming a relatively large vapor bubble (FIG. 1B). After the bubble rapidly expands and the water vapor comes in contact with much colder surrounding water (e.g., about 37° C.), it re-condenses in a few microseconds, and disappears. The re-condensation process typically takes less than 30 vs. Very small bubbles of ex-solved $N_2$ and/or $O_2$ may be seen, which linger at the site of the vapor bubble until these gases re-dissolve into solution, typically after about 1 s (FIG. 1C). The rapid radial flow caused by the phase explosion drags objects such as cells away from the phase explosion center, with fluid velocities reaching about 10 m/s.

Figure 2:
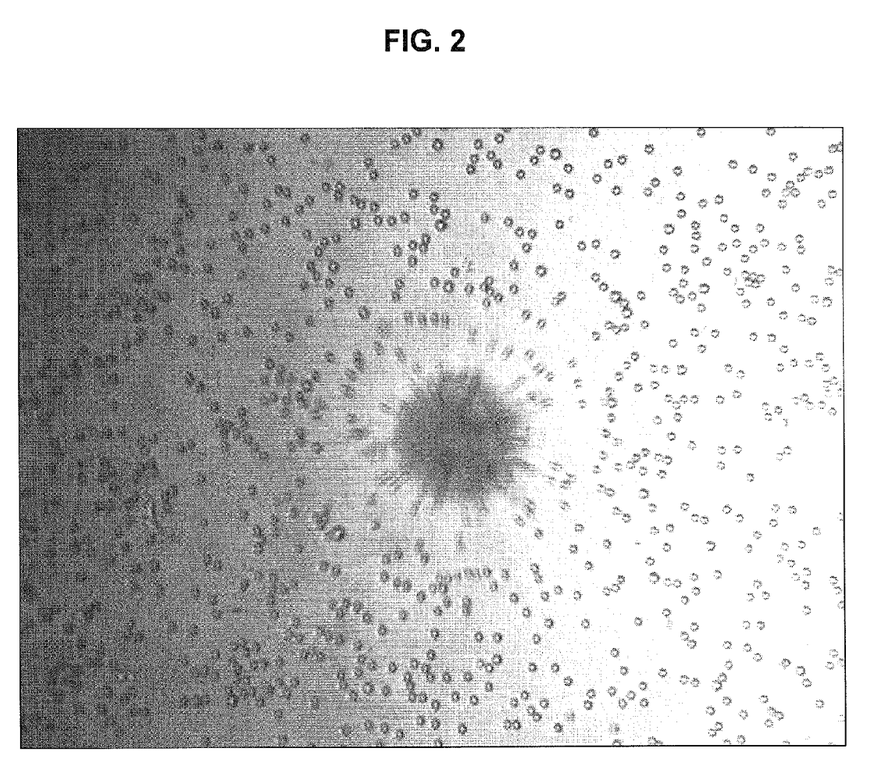
FIG. 2. Stroboscopic image of a phase change vapor bubble just after its formation in a suspension of 4 μm diameter microspheres. The microscope is focused on the PBP bubble, which is slightly above the floor of the dish; the beads on the floor are therefore slightly defocused.
Figure 3:
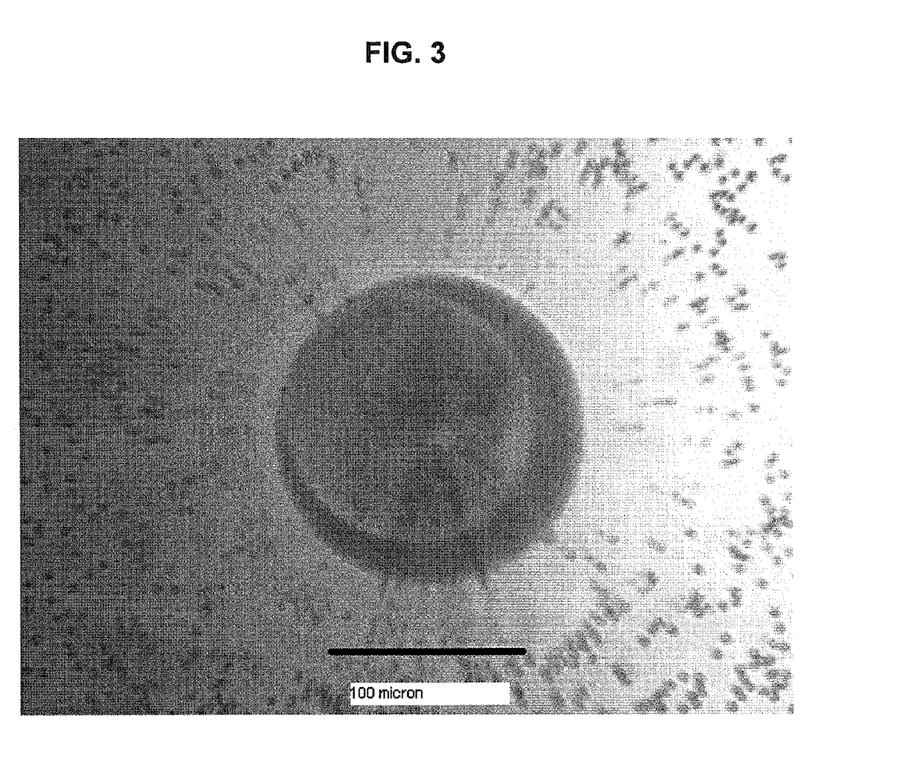
FIG. 3. Stroboscopic image of a phase change vapor bubble near the maximum radius. (Scale bar=100 μm).

Phase boundary propulsion is too rapid to be seen during normal observation of a target, but its formation and effects can be studied directly, for example using a stroboscopic Xe flashlamp. FIG. 2 shows a stroboscopic microscope image of a developing PBP in an aqueous medium containing 4 µm latex beads. Even at the earliest stages of formation of the vapor bubble, outward radial movement of the microbeads is visible. The water vapor bubble typically reaches its maximum radius (FIG. 3) in less than 10 µs. Based on calculations made by analyzing a series of images, the expansion velocity of the vapor bubble is about 10 m/s. This is well below the speed of sound, so no shock wave is formed, but the motion of the phase boundary exerts sufficient force to cause surrounding water and microbeads to move away from the path of the beam. In this regard, phase boundary propulsion can push cells away from the laser beam focus in an action similar to the bow-wave formed by a ship.

The properties of phase boundary propulsion are consistent with the predicted behavior of phase transitions associated with superheated water. The superheated water volume increases quasi-linearly with increasing pulse time. It is found that the greater the latency (the time taken for the phase boundary expansion process to initiate), the more thermal energy has been stored, and the larger the PBP bubble will become once formed. Direct measurements indicate that the maximum diameter of the vapor bubble will increase approximately as the cube root of the latency interval, as expected.

PBP effects described herein generate sufficient hydrodynamic forces to move nearby objects, such as cells, without causing the damage that could accompany a true shockwave. Importantly, these forces are generated by phase boundary propulsion rather than by direct laser heating.

The embodiments of the invention described herein take advantage of the capacity of water to briefly store energy and release it in a sudden phase change. This is accomplished by heating the liquid more rapidly than the heat can diffuse away. The invention further takes advantage of the fact that water has significant temperature dependence in its IR absorption properties. By selecting appropriate wavelengths, the probability of producing PBP can be greatly enhanced.

A preferred embodiment of the present invention provides a method for disrupting cell colonies or cutting biological material using a Class I laser, an inverted microscope equipped with optics adapted for efficient infrared laser beam transmission, and computer-aided stage motion. This embodiment can be used to produce repeated, controlled phase boundary propulsion events as the medium changes from superheated water to vapor. These events create hydrodynamic forces sufficient to reposition nearby objects like cells without significantly heating them. The inventions described herein therefore differ fundamentally from conventional laser cutting, in which a target is thermally weakened, melted or evaporated.

The present invention provides for lower energy lasers delivering longer duration pulses of lower intensity than known UV laser-based microdissection systems. The wavelengths for lasers described herein are preferably within the eye-safe range, and more preferably within the $1400 < \lambda < 1500$ nm range. Suitable lasers also possess power output levels that fall within the Class I criteria.

In an exemplary embodiment of the present invention, an InGaAsP diode infrared laser is used, having an output wavelength, λ, of about 1450 nm, or preferably $1400 < \lambda < 1450$ nm, and most preferably $1410 \leq \lambda \leq 1430$ nm. Alternatively, the output wavelength of $1850 \leq \lambda \leq 1920$ nm. The laser is capable of delivering pulses in a repetitive mode. The maximum number of pulses and pulse rate permissible while operating in this mode are preferably the maximum allowable to maintain laser Class I status. Class I limits for eye and skin exposure to radiation with $\lambda > 1400$ nm (e.g., λ=1450 nm) are typically about 100 mW/cm² for continuous wave irradiation, and higher for pulsed wave beams. It is preferred that mean power of the system be kept below 90 mW in the repetitively pulsed mode.

Exemplary laser-objective systems suitable for the functions described herein may comprise a laser having an output of λ near 1450 nm, which at room temperature has an absorptivity κ of about 28 cm$^{-1}$ and an optical depth of about 360 µm, and an objective lens. This allows more than 100 µm for focus distance between floor and sample, while allowing high energy density to be applied to the target. In some embodiments, it may be preferred to have the laser-objective system operate together as a permanently coupled system for delivering infrared radiation to the sample. However, for some applications or purposes, it may be preferred to have the laser-objective system be comprised of interchangeable series (e.g., mix-and-match) of lasers and objectives.

Two exemplary preferred objectives useful in the present invention are 20× magnification (focal length=10 mm) and 40× magnification (focal length=5 mm). It is preferred that the numerical aperture (NA) be larger than that actually used for the laser, since the collimated laser beam incident on the objective back lens does not fill the 5 mm lens diameter, and is typically about 2 mm in diameter. The corresponding effective beam diameters for the 20× and 40× objectives are approximately 3 and 2 mm, respectively, and the effective numerical apertures (measured in air) are estimated at NA=0.15 and 0.2, respectively.

In a particularly preferred embodiment, the laser-objective system described herein is used in conjunction with a microscope. The laser-objective system is fitted onto the turret of the microscope, with the infrared beam reflected from a 45° dichroic mirror, and travels through the objective onto the target. The dichroic mirror is designed to reflect IR wavelengths and transmit visible wavelengths, and can reflect the IR beam from the laser to the specimen on the microscope stage, while permitting visible light to pass straight through the mirror to the microscope eyepiece or to an attached camera. In this way, the same optical path can be used for laser manipulation and viewing the specimen without the danger of laser light reaching the eye.

EXAMPLES

Example 1

Repeated Pulses in the Same Location

If a laser beam of power P is directed for a time $t_0$ at a liquid target, then, ignoring convection, the temperature T at the beam center after time t (for t>>$t_0$) is approximately given by equation (1):

$$T = \frac{\alpha P t_0}{4\pi K t} \quad (1)$$

where α is the absorption coefficient of the liquid target and K is the thermal conductivity.

If n pulses are added each after interval t, the approximate temperature at the beginning of the n$^{th}$ pulse is given by equation (2):

$$T = \frac{\alpha P t_0}{4\pi K} \sum_1^n \left(\frac{1}{t}\right) \quad (2)$$

Therefore if the laser spot is moved only slightly between laser firings, and if the interval between laser shots is about 10 ms, the subsequent laser shots will travel through liquid that is already heated from the previous shots. For wavelengths 1410<λ<1430 nm, the absorption coefficient (α) increases with temperature, and the absorption of the second and subsequent pulses will be higher than for the first pulse. The effect of these properties is that subsequent PBP bubble formation will be facilitated once a first PBP has occurred. The result is that as the multipulse beam travels it reinitiates PBP at each new position, allowing particles to be swept aside from the beam focus as it moves.

Example 2

Repeated Pulses in a Moving Sample

Figure 4:
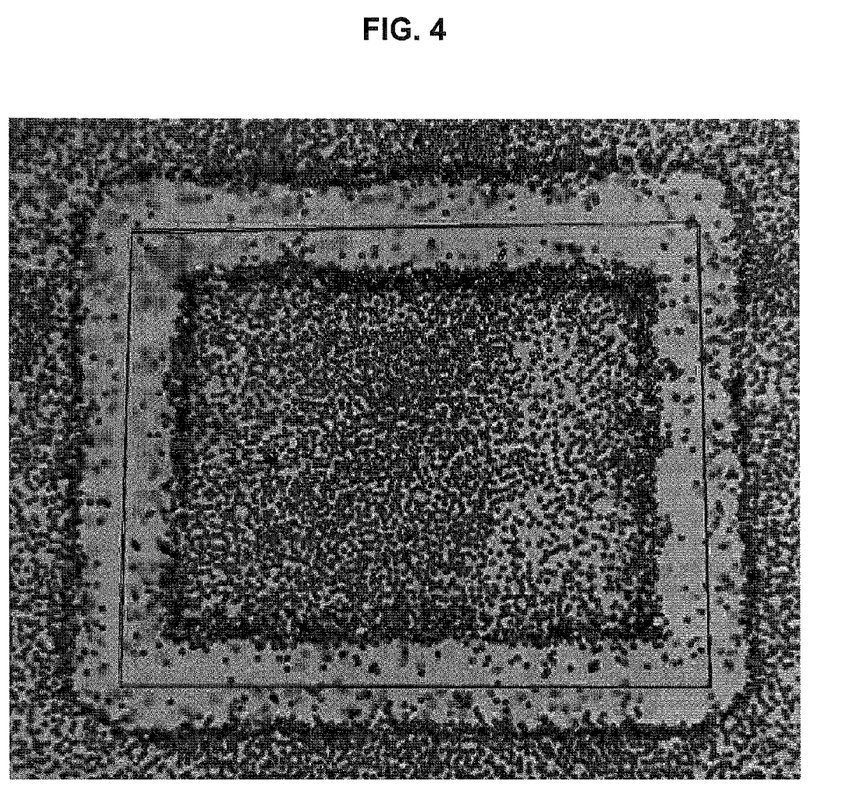
FIG. 4. Track cut through layer of 4 μm diameter microspheres (polystyrene beads) in water, using a 20× objective.

In a preferred embodiment of the invention, phase boundary propulsion generated by the laser-objective system is used in a multipulse mode for cell cutting. In this embodiment, repeated pulses are delivered at 100-1000 Hz, preferably about 100-200 Hz, and moving the focal point through the medium produces a series of adjacent PBP bubbles. The effect of this movement through a cell colony is to sweep aside cells and to leave a large, clear separation between the two sides of the colony bisected by the beam path. This effect is illustrated in FIG. 4, which shows an image obtained using 4 µm beads in a Petri dish on a computerized stage. The stage is programmed to move so that the laser focus follows the rectangular pattern indicated by the thin line, but any arbitrary shape or position is possible. The width of the cut varies directly with latency time because increasing latency time increases the stored energy and the phase boundary propulsion vapor bubble volume. As shown, the phase explosions produced by the laser move the beads regularly to each side and do not leave gaps. The area followed by the beam is clear of beads (except for a few which later settled there), which are swept to either side of the beam hydrodynamically and are seen piled up on the edges of the track.

A potential difficulty with traveling PBP bubbles is to ensure that propulsive bursts initiate sequentially as the focused beam is moved through the target area. In general, PBP is not produced if the beam is focused in the medium in free space, distant from the surface of the dish, even using relatively high power (e.g., 400 mW). The PBP requires time to build up sufficient superheated water (which depends strongly on α), and initiation occurs much more readily adjacent to a boundary.

Phase boundary propulsion can be clearly distinguished from direct laser-produced convection that may be caused by heating parcels of medium. These convective heating effects may be produced by using a longer pulse duration and lower intensity beam, which heats up the medium without causing any phase change. However, convection alone cannot produce a clear track cut through the cell colony, with cells being swept away from the laser track. This cell movement requires the hydrodynamic forces produced by sudden phase boundary expansion.

Example 3

Double Pulse Initiation

In some embodiments, a PBP bubble may be initiated by first heating the medium to superheated levels with a long low-power IR pulse, then using a very short high-power pulse to induce a discontinuity in the heated region at the precise time required. Precision is obtained by separating the energy transfer and triggering mechanisms of the laser-objective system.

A double pulse initiation method can benefit from another laser operating alongside the primary laser-objective system described herein. While an intense very short picosecond or femtosecond pulse from a UV laser operating at 337 nm could produce a small vapor bubble and trigger phase expansion, the complications of such a system in terms of cost and safety vitiates the advantages conferred by the small and simple devices disclosed according to the present invention.

Other initiation wavelengths are possible and more useful, however. Water absorbs infrared radiation particularly well at a wavelength of about 3 µm. However, laser light at this wavelength is hardly transmitted through most glasses, and constructing a microscope to accommodate this part of the IR spectrum presents significant challenges. Another peak of water energy absorption occurs at 1.9-2.1 µm, therefore a brief intense pulse at 1.9 µm after prior irradiation at 1450-1490 nm could initiate the phase change necessary to release energy stored in superheated water created by the 1450 nm laser. A similar trigger could be obtained for example with $1410 \leq \lambda \leq 1430$ nm, for example, $\lambda=1420$ nm. By adjusting the time between the pulses and the intensities of the two laser pulses, the phase change process can be controlled.

Double pulse initiation methods using two or more lasers, or irradiating with light of two or more wavelengths, to produce separate superheating and phase transition triggering events are therefore specifically within the scope of the present invention.

Example 4

Cell Viability

Retinal epithelial cells and human stem cells grown on a mouse fibroblast substrate were used to test cell viability. The phase boundary propulsion laser is able to cut a colony into separate patches relying on the hydrodynamic force exerted on its surroundings and not by thermal ablation. Cell viability was assessed by staining cells simultaneously with two fluorescent DNA-binding dyes: Hoechst 33342, a membrane permeant blue dye, and propidium iodide (PI), a membrane impermeant red dye. Viable cells will absorb Hoechst 33342 but not PI, and will appear blue. Non-viable cells, on the other hand, have damaged membranes that permit PI to penetrate the cell and bind to DNA, and will appear red. Cell viability can therefore be determined by comparing the number of red cells to the total number of cells in the sample.

Figure 5:
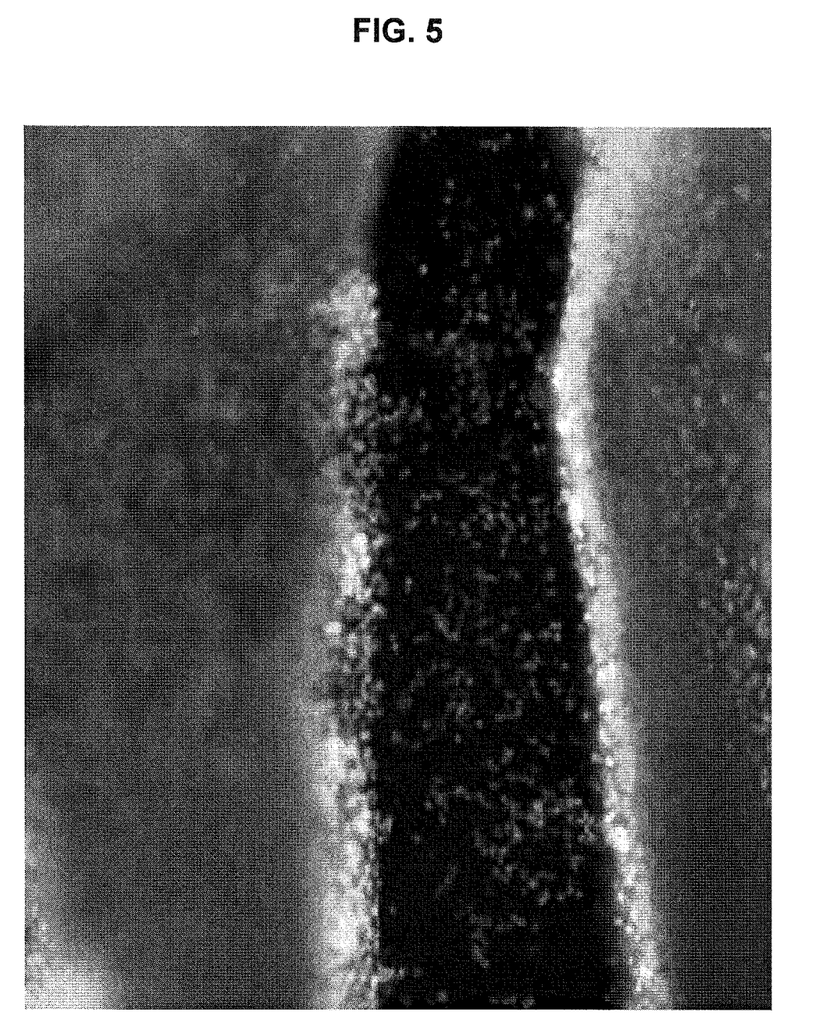
FIG. 5. Track cut through a thick colony of retinal epithelial cells stained with Hoechst 33342 and propidium iodide. All cell nuclei are stained with Hoechst 33342 (blue); membrane-damaged cells are stained with propidium iodide (red).
Figure 6:
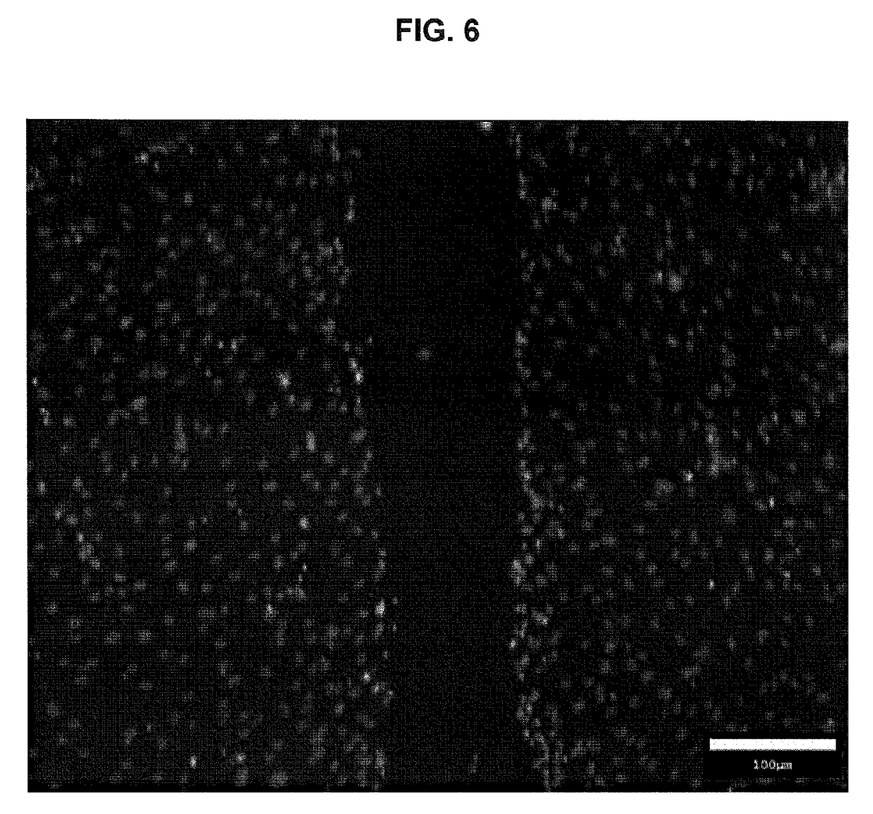
FIG. 6. Track cut through a thin layer of retinal epithelial cells stained with Hoechst 33342 and propidium iodide. (Scale bar=100 μm).

A laser focal diameter of <5 µm was capable of sweeping a track out of a relatively thick (FIG. 5) and thin (FIG. 6) cell layer by creating a hydrodynamic wave resulting from PBP. In each case, the track swept out was roughly 50-100 µm wide. Cell labeling indicated that the vast majority of cells were simply swept away and not damaged. While cells remaining in the open part of the track (e.g., cells that were within <1 µm of the path of the laser spot) are non-viable, cells on the side walls in the thick cell mass pushed aside by PBP appear intact. Other experiments have shown that these cells are functional and capable of freely multiplying in culture (comparable to cells mechanically passaged with a glass pipet; improved compared to cells passaged using trypsin treatment). Gene expression and karyotype analyses have indicated further that cells passaged in this way have normal transcription and translation, and are genetically stable. In the thin cell mass, almost no non-viable cells were found after laser cutting. This result indicates that cell cutting (e.g., for passaging mammalian cell cultures) can be achieved through a mechanism that does not involve thermal ablation, and is produced by the hydrodynamic forces created from controlled phase boundary propulsion.

Moreover, selective membrane permeation/compromise by PBP (e.g., of cells directly in the laser beam) can be exploited, for example to transfect (incorporate exogenous DNA into) cells, or for mass ablation (to isolate cells post-transfection, remove contaminating cells in culture, etc.). In the latter application, PBP can be used to eliminate cells either within a designated area, leaving outside untouched, or outside of that area, leaving inside untouched. This elimination can be achieved, for example, by programming the laser to cover the designated area with a small distance between each path, so that the floor is covered in a closed grid, and every cell is either detached from other cells and from the floor of the chamber and removed, or is run over and killed by the laser beam. Experiments have shown that grids having spacing between 15×15 µm and 30×30 µm could be used for such ablation, whereas grids between 35×35 µm and 40×40 µm allow a minimum number of cells within the grid squares to survive, and grids larger than 40×40 µm (e.g., 100×150 µm, 200×300 µm) could be used for cell passaging.

While there have been shown and described fundamental novel features of the invention as applied to the preferred and exemplary embodiments thereof, it will be understood that omissions and substitutions and changes in the form and details of the disclosed invention may be made by those skilled in the art without departing from the spirit of the invention. Moreover, as is readily apparent, numerous modifications and changes may readily occur to those skilled in the art. Hence, it is not desired to limit the invention to the exact construction and operation shown and described and, accordingly, all suitable modification equivalents may be resorted to falling within the scope of the invention as claimed. It is the intention, therefore, to be limited only as indicated by the scope of the claims appended hereto.

The invention claimed is:

1. A method of repositioning one or more of a plurality of cells suspended in an aqueous medium by inducing phase boundary propulsion (PBP) at a focal point in the aqueous medium, comprising providing infrared energy having a wavelength greater than 1400 nm and an energy less than 1.6 mJ per pulse from a laser through an objective lens to the aqueous medium, superheating the aqueous medium and inducing a phase transition at a temperature insufficient to produce significant ionization, moving the focal point through the medium, and repeating said step of providing the infrared energy, to produce a series of adjacent PBP bubbles.

2. The method of claim 1, wherein said step of providing comprises providing repeated pulses at 100 to 1000 Hz.

3. The method of claim 2, wherein said step of providing comprises providing the repeated pulses at about 100 to 200 Hz.

4. The method of claim 1, wherein said step of providing comprises providing the infrared energy in at least two sequential pulses having different wavelengths, producing separate superheating and phase transition events.

5. The method of claim 1, wherein said step of providing comprises providing the infrared energy in one or more pulses of duration less than 4 ms.

6. The method of claim 1, wherein said step of providing comprises providing the infrared energy in one or more pulses of duration between 50 and 500 µs.

7. The method of claim 1, wherein said step of providing comprises providing the infrared energy in one or more pulses of duration of about 150 µs.

8. The method of claim 1, wherein said step of providing comprises providing the laser energy in repeated pulses having a mean power of less than 90 mW.

9. The method of claim 4, wherein said sequential pulses are provided from separate lasers.

10. The method of claim 4, wherein said sequential pulses comprise a first pulse having a wavelength between 1450 and 1490 nm and a second pulse having a wavelength between 1.9 and 2.1 µm, or between 1410 and 1430 nm.

11. The method of claim 10, wherein the first pulse has a wavelength of about 1450 nm.

12. The method of claim 10, wherein the second pulse has a wavelength of about 1.9 µm.

13. The method of claim 10, wherein the second pulse has a wavelength of about 1420 nm.

14. The method of claim 1, wherein said moving the focal point comprises moving a dish containing the plurality of cells suspended in the aqueous medium on a computerized microscope stage programmed to follow a specified pattern.

* * * * *